United States Patent [19]

Wright

[11] 4,066,769
[45] Jan. 3, 1978

[54] 3,3'-(2,6-PYRIDINEDIYL)DI-5-ISOXAZOLE CARBOXYLIC ACIDS, SALTS, AND ESTERS, COMPOSITIONS AND METHODS OF USE THEREOF

[75] Inventor: John B. Wright, Kalamazoo, Mich.

[73] Assignee: The Upjohn Company, Kalamazoo, Mich.

[21] Appl. No.: 753,719

[22] Filed: Dec. 23, 1976

[51] Int. Cl.² .......................................... C07D 413/14
[52] U.S. Cl. .............................. 424/263; 260/268 H; 260/293.63; 260/294.9; 260/295 R; 544/109
[58] Field of Search ....................... 260/295 R, 294.9; 424/263

[56] References Cited

FOREIGN PATENT DOCUMENTS 228,770  6/1960  Australia ............................. 260/295
1,112,076  8/1961  Germany ............................ 260/295

Primary Examiner—Lorraine A. Weinberger
Assistant Examiner—Lisa Jones
Attorney, Agent, or Firm—Martin B. Barancik

[57] ABSTRACT

Novel compounds of the formula

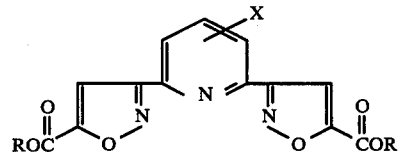

wherein
X is hydrogen, alkyl of one to six carbon atoms, inclusive, alkoxy of one to six atoms, inclusive, phenyl, cyano, nitro, trifluoromethyl, fluoro, chloro or bromo;
R is hydrogen, alkyl of one to eight carbon atoms, inclusive, and a physiologically acceptable metal or amine cation and novel compositions wherein R is hydrogen or a physiologically acceptable metal or amine cation are used for prophylactically treating allergic disorders such as asthma.

20 Claims, No Drawings

3,3'-(2,6-PYRIDINEDIYL-5-ISOXAZOLE CARBOXYLIC ACIDS, SALTS, AND ESTERS, COMPOSITIONS AND METHODS OF USE THEREOF

BRIEF SUMMARY OF THE INVENTION

It has now been discovered that novel compounds of Formula I are useful in the prophylactic treatment of sensitized humans and animals for allergy and anaphylactic reactions of a reagin or non-reagin mediated nature. The compounds are formulated with pharmaceutical carriers for oral, parenteral, inhalation or rectal means of administration.

DETAILED DESCRIPTION OF THE INVENTION

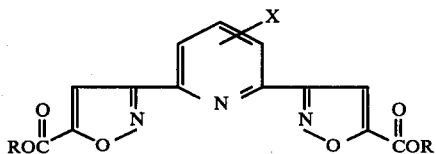

Formula I wherein
X is hydrogen, alkyl of one to six carbon atoms, inclusive, alkoxy of one to six carbon atoms, inclusive, phenyl, cyano, nitro, trifluoromethyl, fluoro, chloro or bromo;
R is hydrogen, alkyl of one to eight carbon atoms, inclusive, and a physiologically acceptable metal or amine cation.

Another group of compounds, hereafter referred to as Group B, are those compounds of Group A wherein R is hydrogen, alkyl of one to six carbon atoms, inclusive, or a physiologically acceptable metal or amine cation; X is hydrogen, alkyl of one to four carbon atoms, inclusive, alkoxy of one to four carbon atoms, inclusive, phenyl, cyano, nitro, trifluoromethyl, fluoro, chloro and bromo.

A further group of compounds, hereafter referred to as Group C, are those compounds of Group B wherein R is hydrogen, alkyl of one to three carbon atoms, inclusive, or a physiologically acceptable metal or amine cation; X is hydrogen, alkyl of one to three carbon atoms, inclusive, alkoxy of one to three carbon atoms, inclusive, phenyl, cyano, trifluoromethyl, fluoro, chloro or bromo.

Another group of compounds, hereafter referred to as Group D, are those compounds of Group C wherein X is hydrogen, alkyl of one to three carbon atoms, inclusive, alkoxy of one to three carbon atoms, inclusive, cyano thrifluoromethyl, fluoro and chloro.

A further group of compounds are those compounds of Group D wherein X is at the four position.

The tris(hydroxymethyl)aminomethane salt of the compound of the formula wherein X is hydrogen is preferred.

As employed in the above disclosure and throughout the specification and claims, the phrase "alkyl of one to eight carbon atoms, inclusive" includes methyl, ethyl, propyl, butyl pentyl, hexyl, heptyl, octyl and isomers thereof. Illustrative examples of isomers are isopropyl, tert.butyl, neopentyl, 2,2-dimethylbutyl, 2-methylhexyl, and 2,2,4-trimethylphentyl. Alkyl of a smaller number of carbon atoms has a similar scoping.

The phrase "physiologically acceptable amine salt" refers to amines which are accepted by mammals in an essentially non-toxic manner when administered to mammals in conjunction with the acid moiety of the invention. Illustrative of the amines are those derived from primary, secondary or tertiary amines. Examples of suitable amines are methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, adamantylamines, and like aliphatic, cycloaliphatic, and araliphatic amines containing up to and including about eighteen carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-1-ethyl-1,3-propanediol, 2-amino-2-methyl-1-propanol, tris(hydroxymethyl)aminomethane, N-phenylethanolamine, N-(p-tert-amylphenyl)diethanolamine, galactamine, N-methylglucamine, N-methylglucosamine, ephedrine, phenylephrine, epinephrine, procaine, and the like. Also included within the amine scope are quaternary amines such as ammonium, tetramethylammonium, tetraethylammonium, benzyltrimethylammonium, phenyltriethylammonium, and the like.

The term "physiologically acceptable metal" includes alkali metals such as sodium and potassium, alkaline earth metals such as calcium and magnesium, and other acceptable metals such as aluminum.

The compounds of the invention can be prepared by methods known in the art.

With respect to the 5-isoxazole carboxylates, acids and salts thereof, the appropriately substituted pyridine dialdehyde (II) is a suitable starting material. These compounds are reacted with an acid addition salt of hydroxylamine, for example, hydroxylamine hydrochloride (III) under standard conditions to form a dioxime (IV). The dioxime is then reacted with a halogen such as chlorine or bromine in an inert organic solvent at a low temperature to form the α,α-dihalopyridyldioxime (V). The product of Formula V is then reacted with an alkyl propiolate (VI) in organic solvent containing an organic base to form the 5-isoxazolecarboxylate.

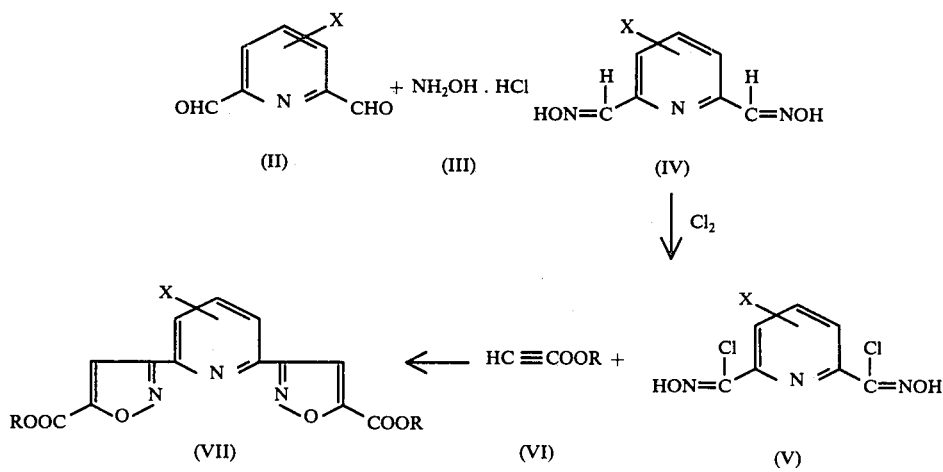

The esters of Formula VII are readily transesterified to other esters of Formula I or converted to the acid or a physiologically acceptable salt by standard methods.

In preparing the 5-isoxazolecarboxylates, the appropriately X substituted aldehydes are prepared by conventional substitution methods. Depending upon the substituent itself, the placement of the aldehyde group, the substitution of the pyridine ring can occur on pyridine itself, pyridine aldehyde, or the pyridine dialdehyde, depending upon the orientation direction effect of the substituent. The appropriately substituted starting material is then reacted with an acid addition salt of hydroxylamine under standard conditions to form the pyridine dioxime. The dioxime is then reacted with a halogen gas, preferably chlorine in an organic solvent inert to the gas of a low temperature to form the $\alpha,\alpha$-dihalopyridyldioxime. Halogenated solvents such as carbon tetrachloride, chloroform and methylene chloride are suitable solvents for the halogenation step. The temperature of the reaction should be maintained from 0° to about 30° C., preferably from 0 to about 15° C. The $\alpha,\alpha$-dihalogenated dioxime is then reacted with an alkyl propiolate, alkyl having one to six carbon atoms, inclusive, in an organic solvent and an amine to form the 5-isoxazolecarboxylate. Suitable organic solvents are lower alcohols such as methanol, ethanol, propanol and the like, and cyclic ethers such as tetrahydrofuran and 1,4-dioxane. Suitable amines functioning as an acid scavenging agent are triethylamine, tripropylamine, and higher trialkylamines, 1-methylpiperidine, 1-methylpyrrolidine, 1,4-dimethylpiperazine and the like.

The diesters are then converted to the diacids by alkaline hydrolysis with a base such as sodium hydroxide followed by treatment with an acid such as hydrochloric acid. The acid is then readily converted into any of the physiologically acceptable metal or amine salts.

Following are illustrative examples of compounds of the invention which can be prepared by the known procedures.

TABLE I

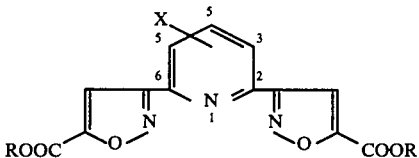

R is $C_2H_5$

| X |
| --- |
| H |
| 4-$CH_3$ |
| 3-i-$C_6H_{13}$ |
| 4-t-$C_4H_9$ |
| 3-$OC_2H_5$ |
| 3-$OC_5H_{11}$ |
| 4-O-i-$C_3H_7$ |
| 3-$OC_2H_5$ |
| 4-$C_6H_5$ |
| 3-$C_6H_5$ |
| 4-CN |
| 3-$NO_2$ |
| 4-$NO_2$ |
| 3-$CF_3$ |
| 4-$CF_3$ |
| 3-F |
| 4-F |
| 3-Cl |
| 4-Cl |
| 3-Br |
| 4-Br |

TABLE II

The compounds of Table I are converted to esters wherein R is alkyl of one to eight carbon atoms, inclusive, other than ethyl. Examples of such esters are methyl, propyl, butyl, pentyl, hexyl, heptyl, octyl and isomers thereof.

TABLE III

The compounds of Table I are converted to the diacids by standard methods.

TABLE IV

The compounds of Table III are converted to physiologically acceptable salts of the acid, preferably sodium, potassium and tris(hydroxymethyl)aminomethane.

Table II, III and IV are not rendered in the same manner as Table I for the purpose of brevity. However, the same scoping is intended.

The following examples are compounds in accordance with this invention and compounds which can be formulated into pharmaceutical compositions of the invention. The compounds are not intended to limit but merely to exemplify the invention. All temperatures are in degrees Centigrade.

EXAMPLE 1

Diethyl 3,3'-(2,6-Pyridinediyl)di-5-isoxazolecarboxylate a. A suspension of 16.5 g. (0.1 mole) of pyridine 2,6-dialdoxime and 200 ml. of carbon tetrachloride is stirred and cooled in an ice-bath. Into the suspension there is bubbled chlorine gas for 3 hours. The ice-bath is removed and the mixture allowed to warm to room temperature. The reaction mixture is allowed to stand overnight.

The insoluble material is removed by filtration. There is obtained 8.13 gm. of material melting at 193° (dec.).

b. A solution of 8.13 g. (0.03 mole) of $\alpha,\alpha'$-dichloropyridine 2,6-dioxime in 200 ml. of ethanol is stirred and there is added 6.47 gm. (0.066 mole) of ethyl propiolate. The solution is cooled in an ice-bath and there is added 10.0 g. (0.099 mole) of triethylamine over a period of thirty minutes. The solution is warmed to room temperature and allowed to stand overnight.

The solution is evaporated to dryness in vacuo. The residue is shaken well into a two phase system of water and ethyl acetate. The phases are separated. The organic phase is washed with water and dried over magnesium sulfate. The drying agent is removed by filtration. The filtrate is evaporated to dryness in vacuo. The residue is recrystallized from ethanol. There is obtained 1.47 g. of a tan solid melting at 135°-138°. From the filtrate there is obtained an additional 1.22 g. of material melting also at 135°-138°. The total yield is 2.69 g. (25%).

Analysis Found: C, 56.98; H, 4.47; N, 11.83%

EXAMPLE 2

3,3'-(2,6-Pyridinediyl)di-5-isoxazolecarboxylic Acid Hydrate

A mixture of 2.5 g. (0.005 mole) of diethyl 3,3'-(2,6-pyridinediyl)di-5-isoxazolecarboxylate and 250 mg. of sodium hydroxide in 50 ml. of water is refluxed for ninety minutes. The reaction mixture is cooled to room temperature and the insoluble material removed by filtration. The filtrate is acidified with concentrated hydrochloric acid. The gelatinous precipitate is removed by filtration and washed with water. There is obtained 610 mg. of a tan solid (38%) melting at 284° (dec.).

Analysis Found: C, 48.95; H, 2.51; N, 13.39%.

The compositions of the present invention are presented for administration to humans and animals in unit dosage forms, such as tablets, capsules, pills, powders, granules, sterile parenteral solutions or suspensions, eye drops, oral solutions or suspensions, and oil-in-water and water-in-oil emulsions containing suitable quantities of the compound of Formula I. The preferred method of administration is by inhalation into the lung or nose by means of an aerosol liquid or powder for insufflation. It should be noted that for composition and methods of using these compositions to prophylactically treat allergy, R is hydrogen or a physiologically acceptable metal or amine cation.

For oral administration, either solid or fluid unit dosage forms can be prepared. For preparing solid compositions such as tablets, the compound of Formula I is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Additionally, a rectal suppository can be employed to deliver the active compound. This dosage form is of particular interest where the mammal cannot be treated conveniently by means of other dosage forms, such as orally or by insufflation, as in the case of young children or debilitated persons. The active compound can be incorporated into any of the known suppository bases by methods known in the art. Examples of such bases include cocoa butter, polyethylene glycols (Carbowaxes), polyethylene sorbitan monostearate, and mixtures of these with other compatible materials to modify the melting point or dissolution rate. These rectal suppositories can weigh from about 1 to 2.5 Gm.

The preferred compositions are those adapted for inhalation into the lung or nose and containing a compound of the invention which is water-soluble. For treatment of allergic conditions of the nose, such as rhinitis, compositions adapted for contact with nasal linings are preferred.

Compositions for inhalation are of three basic types: (1) a powder mixture preferably micropulverized with particle size preferably from about 1 to about 5 microns; (2) an aqueous solution to be sprayed with a nebulizer;

and (3) an aerosol with volatile propellant in a pressurized container.

The powders are quite simply prepared by mixing a compound of the formula with a solid base which is compatible with lung tissue, preferably lactose. The powders are packaged in a device adapted to emit a measured amount of powder when inhaled through the mouth.

Aqueous solutions are prepared by dissolving the compound of the Formula I in water and adding salt to provide an isotonic solution and buffering to a pH compatible with inhalation. The solutions are dispersed in a spray device or nebulizer and sprayed into the mouth while inhaling.

Aerosols are prepared by dissolving a compound of the Formula I in water or ethanol and mixing with a volatile propellant and placing in a pressurized container having a metering valve to release a predetermined amount of material.

The liquefied propellant employed in one which has a boiling point below 65° F. at atmospheric pressure. For use in compositions intended to produce aerosols for medicinal use, the liquefied propellant should be non-toxic. Among the suitable liquefied propellants which may be employed are the lower alkanes containing up to five carbon atoms, such as butane and pentane, or a lower alkyl chloride, such as ethyl, or propyl chlorides. Further suitable liquefied propellants are the fluorinated and fluorochlorinated lower alkanes such as are sold under the trademarks "Freon" and "Genetron". Mixtures of the above-mentioned propellants are dichlorodifluoromethane ("Freon 12"), dichlorotetrafluoroethane ("Freon 11"), dichloromonofluoromethane ("Freon 21"), monochlorodifluoromethane ("Freon 22"), trichlorotrifluoroethane ("Freon 113"), difluoroethane ("Genetron 142-A") and monochlorotrifluoromethane ("Freon 13").

The term "unit dosage form", as used in the specification and claims, refers to physically discrete unit suitable as unitary dosage for human subjects and animals, each unit containing a predetermined quantity of active material calculated to produce the desired therapeutic effect. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, wafers, granules, cachets, teaspoonsful, tablespoonsful, droppersful, ampuls, vials, aerosols with metered discharges, segregated multiples of any of the foregoing, and other forms as herein described.

An effective but non-toxic quantity of the compound is employed in treatment. The dosage of the compound for treatment depends on the route of administration and the potency of the particular compound. A dosage schedule for humans of from about 0.1 to about 20 mg. of compound in a single dose, administered parenterally or by inhalation in the compositions of this invention are effective for preventing allergy attacks. More specifically, the single dose is from about 0.1 to about 5 mg. of compound. The oral and rectal dose is from about 5 to about 50 mg. in a single dose. More specifically, the single dose is from about 10 to about 25 mg. of compound. The dosage to be administered can be repeated up to four times daily. However, when it is necessary to repeat treatment, a preferred dosage schedule reduces the secondary treatment dosage to from about 0.5 percent to about 20 percent of the above dosages, more specifically, from about 1 to about 10 percent of the above dosages. In this manner, a state of allergy prophylaxis can be maintained. The reduced dosage is taken until the dosage no longer provides effective protection. At that time, the larger dosage is repeated, followed by the reduced dosage. An example of such a dosage schedule is the following: An asthmatic individual insufflates 10 mg. of disodio 3,3'-(2,6-pyridinediyl)-di-5-isoxazolecarboxylate. Four hours later, the individual insufflates 0.2 mg. of the same compound and every four to six hours thereafter insufflates 0.2 mg. of the same compound until effective asthma prophylaxis is not provided. The individual then insufflates 10 mg. of the same compound, then reduces the insufflation dosage to 0.2 mg. four to 6 hours later. The dosage schedule continues in this manner.

The administration of the compositions of the present invention to humans and animals provides a method for the prophylactic treatment of allergy or all anaphylactic reactions of a reagin or non-reagin mediated nature. That is to say, these compositions, when administered to a sensitized individual prior to the time that the individual comes into contact with substances (antigens) to which he is allergic, will prevent the allergic reaction which would otherwise occur.

For example, the process can be used for prophylactic treatment of such chronic conditions as bronchial asthma, allergic rhinitis, food allergy, hay fever, urticaria, auto-immune diseases, exercise-induced asthma, stress-induced asthma, systemic anaphylaxis, and bird fancier's disease. Preferred are the reagin mediated conditions such as bronchial asthma, allergic rhinitic, food allergy, and urticaria.

EXAMPLE 3

A lot of 10,000 tablets, each containing 50 mg. of 3,3'-(2,6-pyridinediyl)di-5-isoxazolecarboxylic acid hydrate is prepared from the following types and amounts of ingredients:

| | |
|---|---|
| 3,3'-(2,6-Pyridinediyl)di-5-isoxazolecarboxylic acid hydrate | 500 Gm. |
| Dicalcium phosphate | 1,000 Gm. |
| Methylcellulose, U.S.P. (15 cps) | 60 Gm. |
| Talc | 150 Gm. |
| Corn starch | 200 Gm. |
| Magnesium stearate | 10 Gm. |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets.

These tablets are useful in preventing hay fever attacks at a dose of one tablet every 4 to 6 hours.

EXAMPLE 4

One thousand two-piece hard gelatin capsules, each containing 50 mg. of 3,3'-(2,6-pyridinediyl)di-5-isoxazolecarboxylic acid hydrate are prepared from the following types and amounts of ingredients:

| | |
|---|---|
| 3,3'-(2,6-Pyridinediyl)di-5-isoxazole-carboxylic acid hydrate | 50 Gm. |
| Talc | 50 Gm. |
| Lactose | 100 Gm. |
| Magnesium stearate | 1 Gm |

The ingredients are mixed well and filled into capsules of the proper size.

Capsules so prepared are useful in preventing attacks of bronchial asthma at a dose of one capsule every 4 to 6 hours.

EXAMPLE 5

One thousand tablets, each containing 5 mg. of 3,3'-(2,6-pyridinediyl)di-5-isoxazolecarboxylic acid hydrate are prepared from the following types and amounts of ingredients:

| | |
|---|---|
| 3,3'-(2,6-Pyridinediyl)di-5-isoxazole-carboxylic acid hydrate | 5 Gm. |
| Microcrystalline cellulose NF | 410 Gm. |
| Starch | 100 Gm. |
| Magnesium stearate powder | 3 Gm. |

The ingredients are screened and blended together and pressed into tablets.

The tablets are useful to protect against food allergy at a dose of one tablet before meals.

EXAMPLE 6

One thousand tablets, each containing 20 mg. of 3,3'-(2,6-Pyridinediyl)di-5-isoxazolecarboxylic acid hydrate are prepared from the following types and amounts of ingredients:

| | |
|---|---|
| 3,3'-(2,6-Pyridinediyl)-di-5-isoxazole-carboxylic acid hydrate | 20 Gm. |
| Microcrystalline cellulose NF | 410 Gm. |
| Starch | 100 Gm. |
| Magnesium stearate powder | 3 Gm. |

The ingredients are screened and blended together and pressed into tablets.

The tablets are useful to protect against food allergy at a dose of one tablet before meals.

EXAMPLE 7

A sterile preparation suitable for intramuscular injection and containing 20 mg. of di-tris(hydroxymethyl)aminomethane (THAM) salt of 3,3'-(2,6-pyridinediyl)-di-5-isoxazolecarboxylic acid in each milliliter is prepared from the following ingredients:

| | | |
|---|---|---|
| diTHAM salt of 3,3'-(2,6-Pyridinediyl)di-5-isoxazolecarboxylic acid | 20 | Gm. |
| Benzyl benzoate | 200 | ml. |
| Methylparaben | 1.5 | Gm. |
| Propylparaben | 0.5 | Gm. |
| Cottonseed oil q.s. | 1,000 | ml. |

One milliliter of this sterile preparation is injected for prophylactic treatment of allergic rhinitis or urticaria.

EXAMPLE 8

Six hundred ml. of an aqueous solution containing 5.0 mg. of the diTHAM salt of 3,3'-(2,6-pyridinediyl)di-5-isoxazolecarboxylic acid per ml. is prepared as follows:

| | | |
|---|---|---|
| diTHAM salt of 3,3'-(2,6-pyridinediyl)di-5-isoxazolecarboxylic acid | 3.0 | Gm. |
| Sodium chloride | 5 | Gm. |
| Water for injection q.s. | 600 | ml. |

The THAM salt and sodium chloride are dissolved in sufficient water to make 600 ml. and sterile filtered.

The solution is placed in nebulizers designed to deliver 0.25 ml. of solution per spray.

One spray of the solution is inhaled into the lungs every four to six hours for prevention of asthmatic attacks.

EXAMPLE 9

A powder mixture consisting of 2 grams of disodio 3,3'-(2,6-pyridinediyl)di-5-isoxazolecarboxylic acid and sufficient lactose to make five grams of mixture is micropulverized and placed in an insufflator designed to deliver 50 mg. of powder per dose.

One dose of the powder is inhaled into the lungs every 4 to 6 hours for prevention of asthmatic attacks.

The powder is inhaled intranasally every four hours for prevention of rhinitis.

EXAMPLE 10

Twelve grams of an aerosol composition are prepared from the following ingredients:

| | |
|---|---|
| diTHAM salt of 3,3'-(2,6-pyridinediyl)di-5-isoxazolecarboxylic acid | 1.00 Gm. |
| Freon 12 | 1.44 Gm. |
| Freon 114 | 2.16 Gm. |
| Water | 6.80 Gm. |
| Sorbitan monooleate | 0.60 Gm. |

The THAM salt is dissolved in the water and added to the Freons. The twelve grams of compositions are added to a 13 cc plastic coated bottle and capped with a metering valve. The metering valve releases 80 mg. of composition in an aerosol. 80 mg. of the aerosol is inhaled every four to six hours for prevention of asthmatic attacks.

EXAMPLE 11

In individuals who require continual treatment in the Example 3 through 10, the dosage of the Example is given initially and each succeeding administration of the drug is at 1/50 of the initial dosage. This maintenance dosage is continued until effective allergy prophylaxis is not obtained. The initial dosage of Examples 3 through 10 is then started once more, followed by the maintenance dosages.

EXAMPLE 12

After allowing for the different solubilities of the compounds and the activity of the particular compounds as measured, for example, by the in vivo rat passive cutaneous anaphylaxis assay, a suitable quantity of each of the compounds of Tables III and IV is substituted for the active compound in the compositions and uses of Examples 3 through 11. Results showing anti-allergy activity are obtained.

EXAMPLE 13

The rat passive cutaneous anaphylaxis assay is executed in the following manner:

Female Sprague-Dawley 250 gm. rats are skin-sensitized with rat anti-ovalbumin homocytotropic antibody that is heat labile that is heat labile and has a passive cutaneous anaphylaxis titer of 1:128. After a 72-hour latency period, the animals are challenged i.v. with 4 mg. ovalbumin (OA) + 5 mg. Evans blue dye and the test compound. Where the test compound is insufficiently soluble in an appropriate vehicle to be administered i.v., the compound is administered orally from 5 to 6 minutes prior to antigen challenge. Thirty minutes later the extravascular bluing that results from antigen antibody combination at the skin site is used. Antibody dilutions are used such that in control animals a 4 mm spot is the lowest detectable spot, and 4 or 5 lower dilutions are used to give a range of antibody in each animal. Four to five animals are used for each variable in the experiment. Percent inhibition of the PCA assay is calculated by comparing the spot scores of treated rats with the spot scores of control rats. The spot score is the total number of detectable spots divided by the number of animals.

Ditris(hydroxymethyl)aminomethane salt of 3,3'-(2,6-pyridinediyl)di-5-isoxazolecarboxylate is tested intravenously by the above procedure. An effective inhibition is achieved with 1.0 mg./kg. of compound.

I claim:

1. A compound of the formula

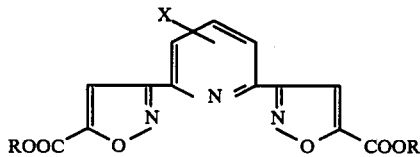

wherein
X is hydrogen, alkyl of one to six carbon atoms, inclusive, alkoxy of one to six carbon atoms, inclusive, phenyl, cyano, nitro, trifluoromethyl, fluoro, chloro or bromo;
R is hydrogen, alkyl of one to eight carbon atoms, inclusive, and a physiologically acceptable metal or amine cation.

2. A compound in accordance with claim 1 wherein R is hydrogen, alkyl of one to six carbon atoms, inclusive, or a physiologically acceptable metal or amine cation;
X is hydrogen, alkyl of one to four carbon atoms, inclusive, alkoxy of one to four carbon atoms, inclusive, phenyl, cyano, nitro, trifluoromethyl, fluoro, chloro and bromo.

3. A compound in accordance with claim 2 wherein R is hydrogen, alkyl of one to three carbon atoms, inclusive, or a physiologically acceptable metal or amine cation;
X is hydrogen, alkyl of one to three carbon atoms, inclusive, alkoxy of one to three carbon atoms, inclusive, phenyl, cyano, trifluoromethyl, fluoro, chloro or bromo.

4. A compound in accordance with claim 3 wherein X is hydrogen, alkyl of one to three carbon atoms, inclusive, alkoxy of one to three carbon atoms, inclusive, cyano, trifluoromethyl, fluoro or chloro.

5. A compound in accordance with claim 4 wherein X is at the four position.

6. Diethyl 3,3'-(2,6-pyridinediyl)di-5-isoxazolecarboxylate according to claim 1.

7. 3,3'-(2,6-Pyridinediyl)di-5-isoxazolecarboxylic acid hydrate according to claim 1.

8. A pharmaceutical composition which comprises an effective amount for the prophylaxis of a reagin mediated allergy of a compound of the formula

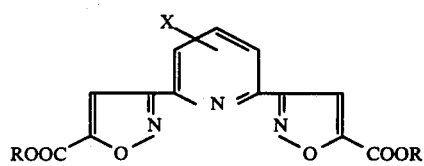

wherein
X is hydrogen, alkyl of one to six carbon atoms, inclusive, alkoxy of one to six carbon atoms, inclusive, phenyl, cyano, nitro, trifluoromethyl, fluoro, chloro or bromo;
R is hydrogen or a pharmaceutically acceptable metal or amine cation, in association with a pharmaceutical carrier.

9. A composition in accordance with claim 8 wherein X is hydrogen, alkyl of one to three carbon atoms, inclusive, alkoxy of one to three carbon atoms, inclusive, cyano, trifluoromethyl, fluoro and chloro.

10. A composition in accordance with claim 9 wherein X is at the 4 position.

11. A composition in accordance with claim 8 wherein R is a physiologically acceptable metal or amine cation.

12. A composition in accordance with claim 10 wherein R is a physiologically acceptable metal or amine cation.

13. A composition in accordance with claim 8 wherein the carrier is solid.

14. A composition in accordance with claim 8 wherein the carrier is liquid.

15. A method for the prophylactic treatment of a reagin mediated allergy in a mammal in need thereof which comprises administering to said mammal a compound of the formula

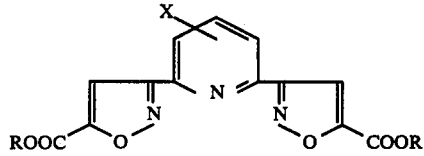

wherein
X is hydrogen, alkyl of one to six carbon atoms, inclusive, alkoxy of one to six carbon atoms, inclusive, phenyl cyano, nitro, trifluoromethyl, fluoro, chloro or bromo;
R is hydrogen or a pharmaceutically acceptable metal or amine cation, in an amount effective to prevent the symptoms of said allergy, in association with a pharmaceutically acceptable carrier.

16. A method in accordance with claim 15 wherein X is hydrogen, alkyl of one to three carbon atoms, inclusive, alkoxy of one to three carbon atoms, inclusive, cyano, trifluoromethyl, fluoro and chloro.

17. A method in accordance with claim 16 wherein X is at the four position.

18. A method in accordance with claim 15 wherein R is a physiologically acceptable metal or amine cation.

19. A method in accordance with claim 17 wherein R is a physiologically acceptable metal or amine cation.

20. 3,3-(2,6-Pyridinediyl)di-5-isoxazolecarboxylic acid according to claim 1.

* * * * *